(12) United States Patent
Young et al.

(10) Patent No.: US 8,216,226 B2
(45) Date of Patent: Jul. 10, 2012

(54) RADIOFREQUENCY ABLATION DEVICE

(75) Inventors: Kimbolt Young, Newtonville, MA (US); Jeffrey W. Zerfas, Bloomington, IN (US); Steve Pickett, Spencer, IN (US); Mohamed Faznl Abdulaziz, Bloomington, IN (US); Gerald M. Hubbs, Bloomington, IN (US)

(73) Assignee: Boston Scientific Scimed, Inc., Maple Grove, MA (US)

( * ) Notice: Subject to any disclaimer, the term of this patent is extended or adjusted under 35 U.S.C. 154(b) by 1129 days.

(21) Appl. No.: 12/099,062

(22) Filed: Apr. 7, 2008

(65) Prior Publication Data
US 2008/0255553 A1  Oct. 16, 2008

Related U.S. Application Data

(60) Provisional application No. 60/911,860, filed on Apr. 13, 2007.

(51) Int. Cl.
*A61B 18/18* (2006.01)
(52) U.S. Cl. ............................................ 606/41; 606/37
(58) Field of Classification Search ..................... 606/41
See application file for complete search history.

(56) References Cited

U.S. PATENT DOCUMENTS

| | | | |
|---|---|---|---|
| 3,174,851 A | | 3/1965 | Buehler et al. |
| 3,351,463 A | | 11/1967 | Rozner et al. |
| 3,753,700 A | | 8/1973 | Harrison et al. |
| 5,281,218 A | * | 1/1994 | Imran ............................. 606/41 |
| 5,551,426 A | * | 9/1996 | Hummel et al. ............. 600/374 |
| 6,016,452 A | * | 1/2000 | Kasevich ...................... 607/101 |
| 6,071,280 A | * | 6/2000 | Edwards et al. ................ 606/41 |
| 6,312,429 B1 | * | 11/2001 | Burbank et al. ................ 606/47 |
| 7,416,549 B2 | * | 8/2008 | Young et al. .................... 606/41 |
| 7,896,874 B2 | * | 3/2011 | Young et al. .................... 606/41 |
| 2002/0095202 A1 | | 7/2002 | Schmidt |
| 2006/0149226 A1 | | 7/2006 | McCullagh et al. |
| 2006/0206111 A1 | | 9/2006 | Young |

FOREIGN PATENT DOCUMENTS

EP  0 629 382 A1  12/1994
(Continued)

OTHER PUBLICATIONS

PCT International Search Report for PCT/US2008/059589, Applicant: Boston Scientific Scimed, Inc., Form PCT/ISA/210 and 220, dated Aug. 6, 2008 (6 pages).

(Continued)

*Primary Examiner* — Linda Dvorak
*Assistant Examiner* — Brian M Antiskay
(74) *Attorney, Agent, or Firm* — Vista IP Lawgroup LLP (57) ABSTRACT

A RF ablation device includes a probe assembly that has an elongate cannula having a lumen disposed interiorly of an external wall of the cannula. The elongate cannula includes a plurality of slots formed within the external wall that provide access to the lumen. The probe assembly includes an electrode member that is slidably disposed within the elongate cannula, the electrode member including a plurality of tines configured for passage through the plurality of slots. The slots are disposed in a staggered arrangement or pattern about the external wall of the cannula. The staggered arrangement of slots may be used in a monopolar or bipolar arrangement of the electrodes on the cannula. A bipolar arrangement of electrodes using the staggered configuration produces larger ablation areas in a shorter period of time as compared to prior designs.

20 Claims, 5 Drawing Sheets

FOREIGN PATENT DOCUMENTS

| WO | WO 2005/037119 A1 | 4/2005 |
|---|---|---|
| WO | WO 2006/104934 A2 | 10/2006 |

OTHER PUBLICATIONS

PCT Written Opinion of the International Search Authority for PCT/US2008/059589, Applicant: Boston Scientific Scimed, Inc., Form PCT/ISA/237, dated Aug. 6, 2008 (7 pages).

Office Action dated Apr. 14, 2010 in European Patent Application No. 08 745 250.4-2305, Applicant: Boston Scientific Limited, (4pages).

PCT International Preliminary Report on Patentability (Chapter I of the Patent Cooperation Treaty) for PCT/US2008/059589, Applicant: Boston Scientific Limited, Form PCT/IB/326 and 373, dated Oct. 22, 2009 (9 pages).

* cited by examiner

{{PAGE_START}}

RADIOFREQUENCY ABLATION DEVICE

RELATED APPLICATION DATA

The present application claims the benefit under 35 U.S.C. §119 to U.S. Provisional Patent Application Ser. No. 60/911,860, filed Apr. 13, 2007. The foregoing application is incorporated by reference into the present application in its entirety for all purposes.

FIELD OF THE INVENTION

The field of the invention generally relates to the structure and use of radio frequency (RF) electrosurgical probes or ablation devices for the treatment of tissue.

BACKGROUND OF THE INVENTION

In the field of oncology, cancer treatment is often performed using radio frequency (RF) ablation techniques. Conventional ablation techniques use an array of RF needles or tines (sometimes referred to as a "tine array"), which may be configured to deploy in a pre-determined shape or pattern for transferring RF energy into surrounding tissue. The needles or tines act as electrodes which are electrically connected to a RF generator. The needles or tines thus transmit RF energy into the surrounding tissue for the thermal coagulation and/or necrosis of tissue. For example, in an undeployed state, tines are positioned at a target area while housed within the lumen of a cannula. The undeployed tine array enclosed within the cannula may be positioned by inserting the cannula through bone and tissue into a target area. Once inserted, the electrode tine array may be deployed by forcing the electrode tines out of a cannula and into the surrounding target tissue. After deployment, RF energy may be transmitted from the electrode tine array to ablate the target tissue, causing heating and eventual necrosis of cancerous or malignant tissue. RF ablation occurs when a high frequency alternating current flows from one electrode to another, completing a current path, causing ionic agitation. Ionic agitation occurs around an active electrode as a result of frictional heating in the tissue surrounding the electrode tines (e.g., electrodes, RF needle probes, and the like) on an array, leading to cell death and necrosis. After ablating the target tissue, the electrode tine array is then retracted into the cannula and the cannula is removed from the target area.

RF ablation probes may be configured in either monopolar or bipolar mode. In monopolar mode, one electrode (e.g., negative) is located within or on a cannula. In order to complete the circuit for RF energy, a separate electrode pad or the like is typically placed on the skin of the patient. Other bipolar-based devices use multiple electrodes or electrode arrays on a single device. For example, the CONCERTO™ needle electrode device (Boston Scientific Scimed, Inc., Maple Grove, Minn.) uses two electrically independent opposing arrays that are contained within an insulated cannula. RF energy passes between the two arrays and heats the tissue surrounding and in between the arrays.

The electrode array may be deployed via a distal end of the cannula. In other configurations, however, the electrode array may emerge from an inner lumen of the cannula via a plurality of holes or passageways located around the periphery of the cannula. With this last configuration, however, the holes or passageways located within the cannula can reduce the structural integrity of the cannula. This is particularly important because the columnar strength of the cannula is important as the device may require considerable pushing force to insert the cannula into the tissue to reach the desired target zone.

There thus is a need for a RF ablation device that is able to deploy an array of electrodes via side-located slots or apertures which at the same time provides the device with high columnar strength. In addition, the device would permit minimal spacing between the tips of the electrodes within the array such that the RF ablation device can efficiently ablate the target tissue.

SUMMARY

In one embodiment of the invention, a RF ablation device includes a probe assembly that includes an elongate cannula having a lumen disposed interiorly of an external wall of the cannula. The elongate cannula includes a plurality of slots formed within the external wall that provide access to the lumen. The probe assembly includes an electrode member that is slidably disposed within the elongate cannula, the electrode member including a plurality of tines configured for passage through the plurality of slots. The slots are disposed in a staggered arrangement or pattern about the external wall of the cannula. The staggered arrangement of slots may be used in a monopolar or bipolar arrangement of the electrodes on the cannula.

In another embodiment of the invention, a RF ablation device includes a probe assembly that has an elongate cannula having a lumen disposed interiorly of an external wall. The elongate cannula includes a plurality of proximally and distally disposed passageways formed within an external wall of the cannula and providing access to the lumen. The plurality of proximal and distal passageways are disposed in a staggered arrangement about the external wall of the cannula. An electrode member is slidably disposed within the elongate cannula, the electrode member including a first plurality of tines configured for passage through the plurality of proximally disposed passageways and a second plurality of tines configured for passage through the plurality of distally disposed passageways. In this configuration, the RF ablation device is configured as a bipolar ablation device.

BRIEF DESCRIPTION OF THE DRAWINGS

The drawings illustrate the design and utility of various embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 2 is a perspective view of a RF ablation probe device according to one aspect of the invention. The cannula portion of the probe device is shown in cross-section. FIG. 2 illustrates the array of electrodes in a retracted state.

FIG. 3 is a perspective view of a RF ablation probe device according to one aspect of the invention. The cannula portion of the probe device is shown in cross-section. FIG. 3 illustrates the array of electrodes in a deployed state.

FIG. 7 illustrates a side view of an RF ablation probe device according to another embodiment. FIG. 7 illustrates a cannula having slots staggered in two separate locations (i.e., a bipolar array) for the active and return electrode arrays.

DETAILED DESCRIPTION

Figure 1:
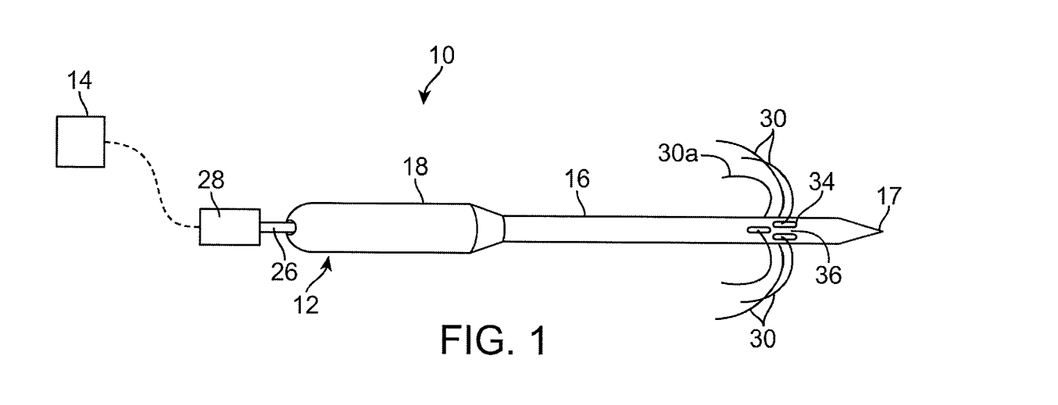
FIG. 1 is a schematic representation of a tissue ablation system according to one aspect of the invention.

FIG. 1 illustrates a radiofrequency (RF) ablation device 10 according to one aspect of the invention. As seen in FIG. 1, the RF ablation device 10 includes probe assembly 12 that is configured for introduction into a body of a patient for ablative treatment of target tissue. The target tissue may include, for example, cancerous tissue located within an organ or body tissue. As one illustrative example, the RF ablation device 10 may be used to ablate cancerous tissue located within liver tissue although the invention is not limited to the type of tissue being ablated. The RF ablation device 10 is coupled to a RF generator 14 configured for supplying RF energy to the probe assembly 12 in a controlled manner.

Figure 2:
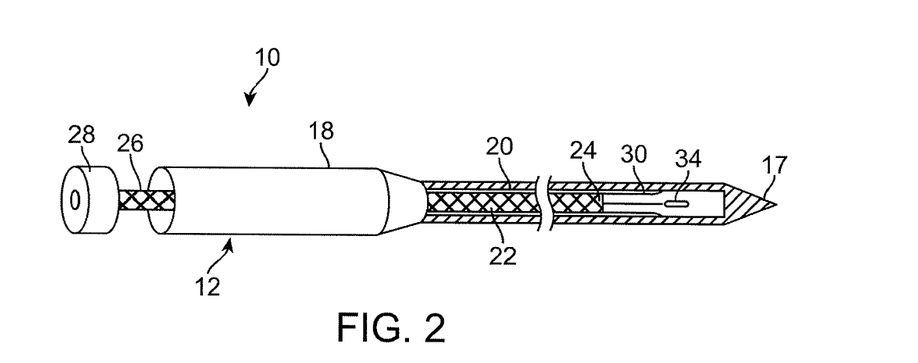
Figure 3:
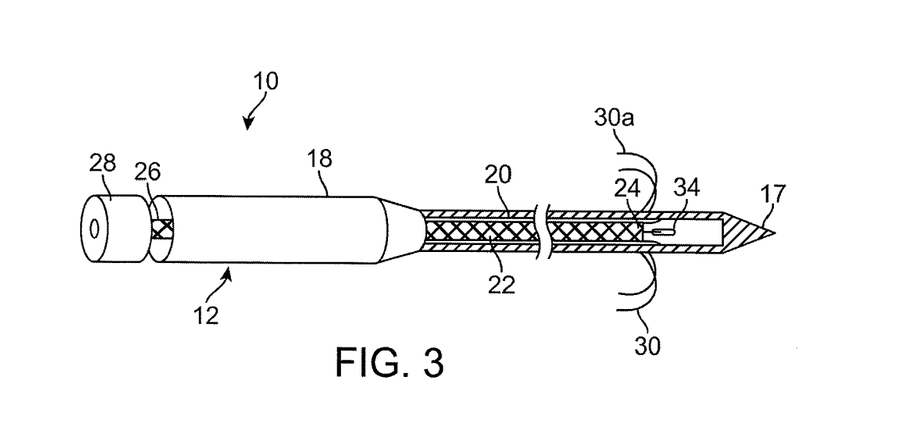

The probe assembly 12 as seen in FIG. 1, includes an elongate cannula 16 that is coupled to a handle 18 or the like that is used to grip the device 10. The elongate cannula 16 may terminate in a sharpened tip 17 as illustrated in FIGS. 1-3. In still other configurations, however, the distal end of the cannula 16 may include an opening or passageway (not shown) that may be used to pass one or more electrodes. As best seen in FIGS. 2 and 3, the cannula 16 includes a central lumen 20 through which passes a slidable electrode member 22 which may take the form of one or more shafts or tubes. The elongate cannula 16 may be made having a rigid construction such that the device 10, when inserted into a target tissue, does not torque, bend, or flex. The elongate cannula 16 may be constructed of a metallic material such as, for example, stainless steel, titanium, NITINOL, or the like. In another aspect, a rigid or stiff polymer or plastic material may be used to construct the elongate cannula 16. The invention is not limited to the type of material used to form the elongate cannula 16. Typically, the cannula 16 is coated or covered with an insulative material.

The cannula 16 may have a suitable length such that the array of electrodes can be positioned to the target region or zone of interest. Typically, the cannula 16 may have a length in the range of around 5 cm to 30 cm although other lengths are contemplated to fall within the scope of the invention. The outer or external wall of the cannula 16 may have an outside, cross-sectional dimension that is consistent with its intended use. For example, the cannula 16 may have an outer diameter (O.D.) within the range of about 0.058 inches (17 gage) to about 0.134 inches (10 gage).

Figure 7:
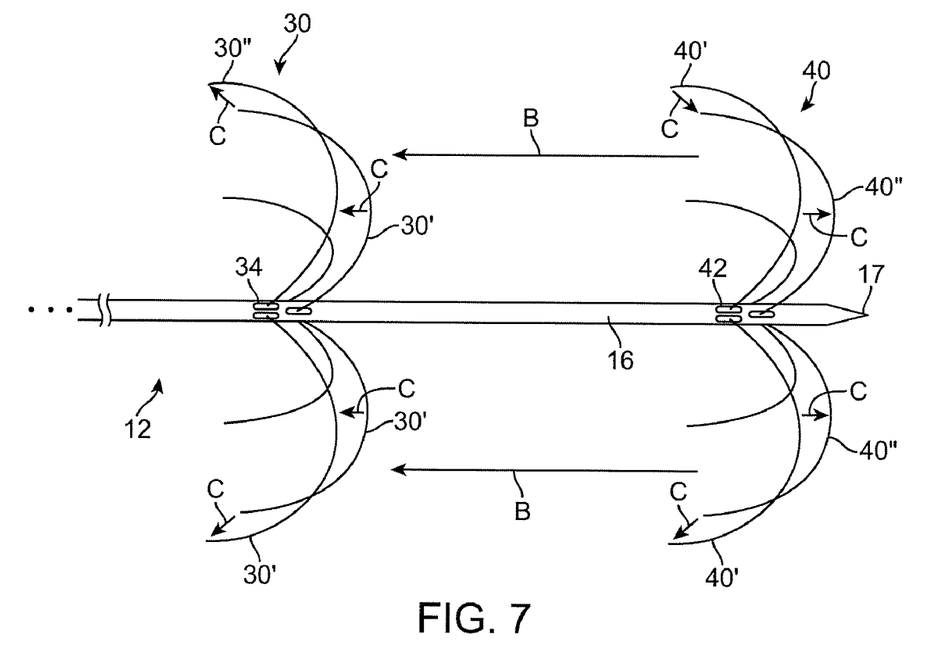
Figure 9:
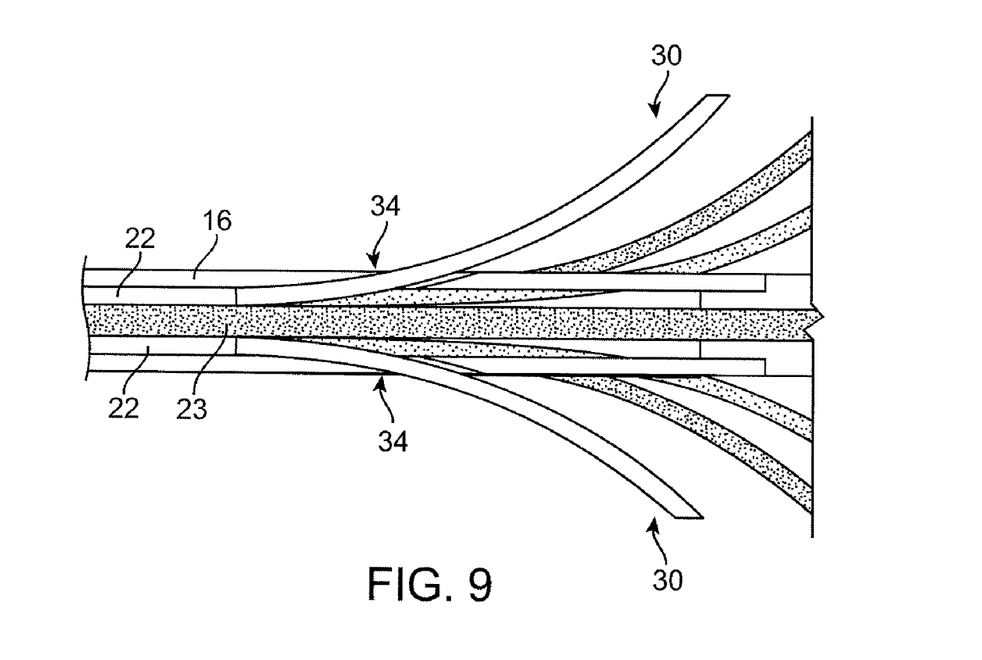
FIG. 9 illustrates a cross-sectional view of segment of cannula having angled or slanted slots arranged in a staggered fashion about the periphery of the cannula. The electrode array is also shown in the deployed configuration, projecting from the cannula.

The electrode member 22 may include a single conductor in the case where the device 10 is run in monopolar mode (e.g., FIGS. 1-3) or, alternatively, the electrode member 22 may include multiple, electrically isolated components that are coupled to respective electrode arrays (described in more detail below). This latter configuration is used for electrodes arranged in the bipolar configuration (e.g., FIGS. 7 and 9). For example, the electrode member 22 may include an outer hollow tubular member (e.g., steel hypotube) that is coupled at a distal end 24 to a proximally arranged electrode array (e.g. as shown in FIGS. 7 and 9).

A second conductor may then be disposed within the interior of the outer hollow tubular member. The second conductor is electrically isolated from the outer hollow tubular member by, for example, an insulative coating (e.g., heat shrink tubing around the second conductor). The distal end of the second conductor may be coupled to a second, distal array of electrodes. The slidable electrode member 22 includes a proximal end 26 that may include a hub 28 or the like that can be manipulated by the physician to selectively deploy the electrode array(s) by sliding the electrode member 22 relative to the cannula 16. In the bipolar mode, the single outer conductor and the centrally disposed second conductor may be moved in unison upon axial movement of the proximal hub 28. Of course, as shown in FIGS. 1-3, the slidable electrode member 22 may include a single conductive member that has an array of electrode tines 30 secured to the distal end 24.

Figure 5:
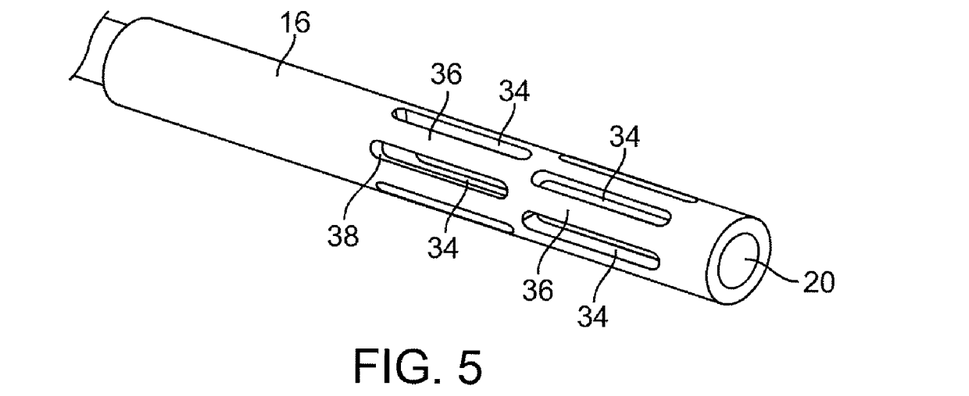
FIG. 5 illustrates a perspective view of a section of cannula illustrating a staggered arrangement of slots about a periphery surface.

With reference to FIG. 1, the cannula 16 has a plurality of staggered passageways 34 located about the periphery of the external wall of the cannula 16. The passageways 34 may be formed, in certain embodiments, as slots that rectangular or oblong in shape. In particular, the slots may have an axial length or dimension that is longer than the width as is shown in FIGS. 1-3, 5, and 7. The passageways or slots 34 are positioned in a staggered orientation about at least a portion of the circumference of the cannula 16. The "staggered" arrangement means that one or more adjacent slots 34 are axially offset from one another. For example, in one aspect of the invention that provides the most structural integrity to the cannula 16, adjacent slots do not overlap one another (in the axial direction). In this regard, relatively substantial and thick struts 36 (as shown in FIG. 5) are located between adjacent slots 34. The thick struts 36 impart columnar strength to the cannula 16 such that the same can avoid twisting, torquing, or bending the cannula 16 during placement.

Figure 4:
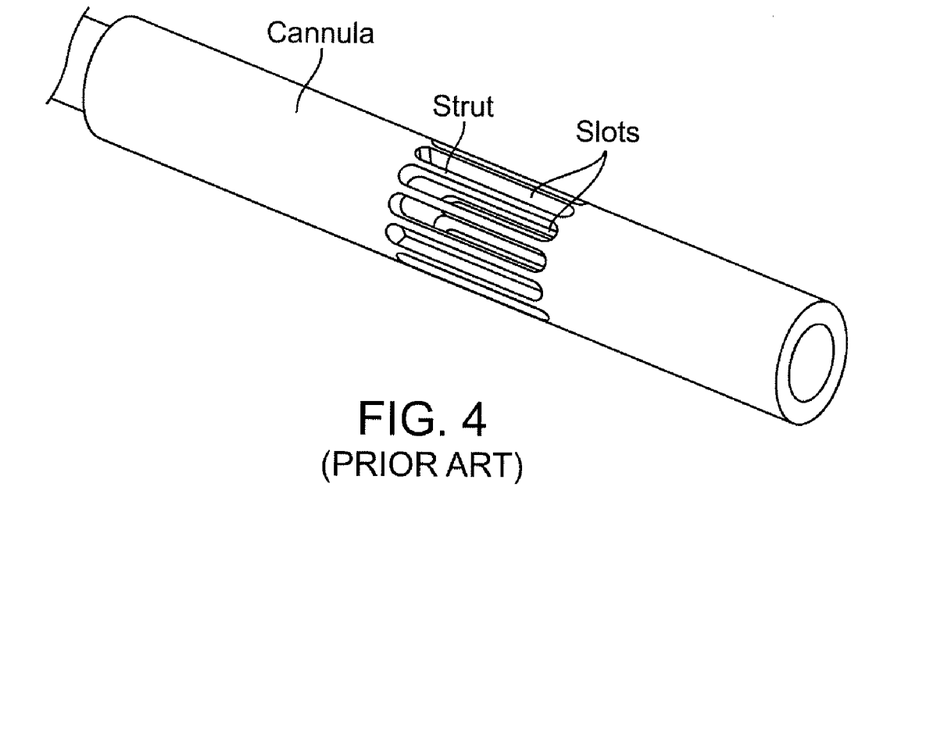
FIG. 4 illustrates a perspective view of a section of cannula illustrating a conventional serial arrangement of slots about a periphery surface.

FIGS. 4 and 5 illustrate the comparison of the increased width of the struts 36 for the staggered design (FIG. 5) as compared to a conventional non-staggered design (FIG. 4) having the same outer diameter (e.g., 0.071 inches). In the construction of FIG. 4 the adjacent slots (12 in total about the circumference) are separated by struts of material having a width of 0.006 inches. In contrast, in the staggered design of FIG. 5, the adjacent slots 34 (also 12 in total) are separated by struts 36 having a width of 0.024 inches. The staggered design thus provides four times the strut width as compared to the conventional design. The staggered design not only provides a way of increasing the columnar strength of the cannula 16 but it also enables the creation of RF ablation devices with very small, narrow diameter cannulas 16. While FIG. 5 illustrates slots 34 that are non-overlapping with one another it should be understood that in certain embodiments, at some or all of the staggered slots 34 may at least partially overlap each other (in the axial direction of the cannula 16).

Figure 6A:
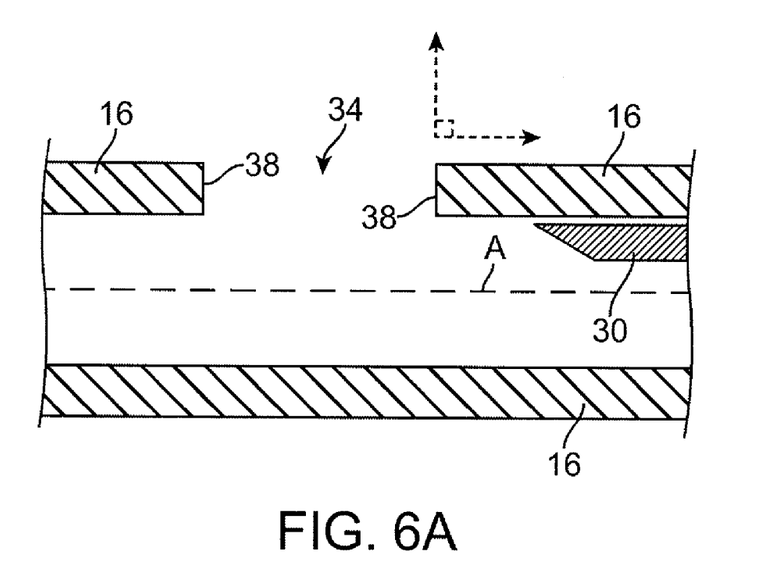
FIG. 6A illustrates a cross-sectional view of a passageway or slot formed in a cannula according to one aspect of the invention.
Figure 6B:
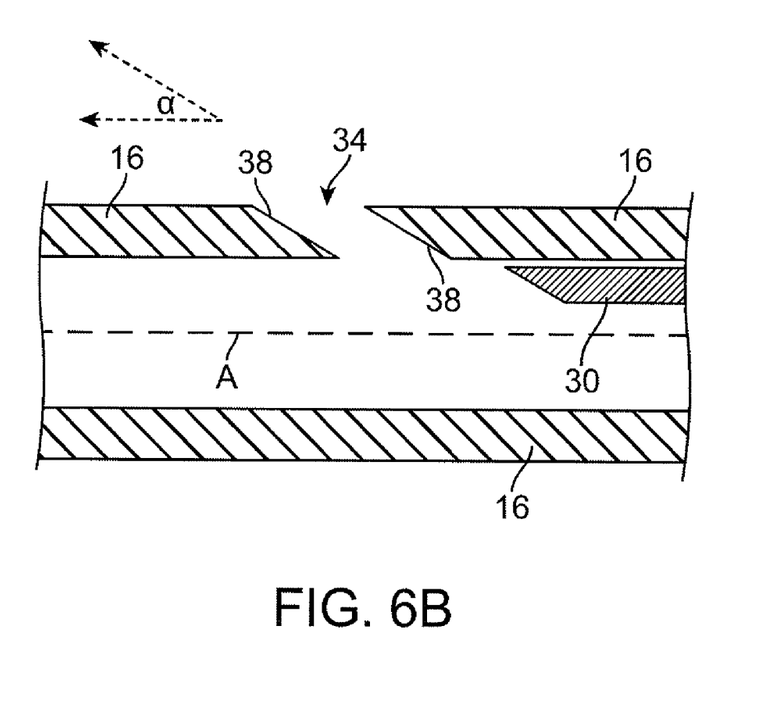
FIG. 6B illustrates a cross-sectional view of a passageway or slot formed in a cannula according to another aspect of the invention.

The staggered slots 34 may be formed within the cannula 16 using any number of processes. For example, the staggered slots 34 may be drilled, milled, or otherwise mechanically formed within cannula 16. The staggered slots 34 may also be formed using radiation energy such as a laser to drill precise passageways. In certain embodiments, like the one illustrated in FIG. 5, the slots 34 are generally oriented perpendicular to the longitudinal axis of the cannula 16. For example, as illustrated in FIG. 6A, the illustrated slot 34 has an interior surface 38 that is oriented substantially perpendicular to the longitudinal axis A of the cannula 16. Alternatively, the slot 34 may include an interior surface that is angled with respect to the longitudinal axis A of the cannula 16. FIG. 6B illustrates a slot 34 that is formed at an angle (α) with respect to the longitudinal axis A of the cannula 16. In this regard, the slots 34 formed in the cannula 16 may be flared, beveled, or otherwise obliquely oriented.

The number of slots 34 formed in the cannula 16 depends on multiple factors including, for example, the particular application in which the RF ablation device 10 is used as well as its size. For example, devices used to ablate relatively large zones or regions may need a larger number of slots 34 to permit passage of a large number of electrode tines. Similarly, smaller-sized devices may require fewer slots 34. In one aspect of the invention, the number of slots 34 that are staggered from one another are equal in number. For example, there may be six (6) slots 34 located on the periphery of the cannula 16 at a first axial position and another six (6) slots 34 located on the periphery of the cannula 16 at a second axial position (i.e., staggered in between the other slots 34). Of course, the invention is not limited to the number of staggered slots 34 positioned about the periphery of the cannula 16.

Referring back to FIGS. 1, 2, and 3, the electrode member 22 terminates in an array of electrode tines 30. It can be appreciated that longitudinal translation of the electrode member 22 (via hub 28) relative to the cannula 16 in the proximal direction causes retraction of the electrode tines 30 within the corresponding slots 34 (as shown in FIG. 2). In contrast, longitudinal translation of the electrode member 22 relative to the cannula 16 in the distal direction causes deployment of the electrode tines 30 out of the corresponding slots 34 (as shown in FIGS. 1 and 3).

As illustrated in FIGS. 1-3, each individual electrodes are formed as electrode tines 30, which resembles the shape of a needle or wire. Each tine 30 is in the form of a slender metal element, which can penetrate into tissue as it is advanced to a target site within the target region. In some embodiments, the distal ends 30a (FIG. 1) of the tines may be honed or sharpened to facilitate their ability to penetrate tissue. The distal ends 30a of these electrode tines 30a may be hardened using conventional heat treatment or other metallurgical processes. They may be partially covered with insulation, although they will be at least partially free from insulation over their distal portions so as to effectuate tissue heating and ablation.

When deployed from the cannula 16, the electrode array 30 has a deployed configuration that defines a volume having a periphery with a radius in the range from around 0.5 cm to around 4.0 cm. It should be understood, however, that other dimensions are contemplated to fall within the scope of the invention. The array of electrodes 30 are resilient and may be pre-shaped or biased to assume a desired configuration when advanced into a target tissue or region of tissue. In the illustrated embodiments, the electrodes 30 diverge radially outwardly from the cannula 16 in a uniform pattern, i.e., with the spacing between adjacent electrodes tines 30 diverging in a substantially uniform and/or symmetric pattern. The electrodes 30 should not be limited to having the profiles shown in FIGS. 1, 3, and 7, and that in alternative embodiments, the electrodes 30 can have different deployed profiles. In certain embodiments, the deployed array 30 may even have a non-symmetrical orientation. It should be noted that although a total of six (6) electrodes tines 30 are illustrated, for example, in FIG. 1, in other embodiments, the probe assembly 12 can have any number of electrode tines 30.

The electrode tines 30 can be made from a variety of electrically conductive elastic materials. Very desirable materials of construction, from a mechanical point of view, are materials which maintain their shape despite being subjected to high stress. Certain "super-elastic alloys" include nickel/titanium alloys, copper/zinc alloys, or nickel/aluminum alloys. Alloys that may be used are also described in U.S. Pat. Nos. 3,174,851, 3,351,463, and 3,753,700, the disclosures of which are hereby expressly incorporated by reference. The electrode tines 30 may also be made from any of a wide variety of stainless steels. The electrode tines 30 may also include the platinum group metals, especially platinum, rhodium, palladium, rhenium, as well as tungsten, gold, silver, tantalum, and alloys of these metals. These metals are largely biologically inert. They also have significant radiopacity to allow the electrode tines 30 to be visualized in-situ, and their alloys may be tailored to accomplish an appropriate blend of flexibility and stiffness. They may be coated onto the electrode tines 30 or be mixed with another material used for their construction.

FIG. 7 illustrates the cannula 16 of another embodiment of a probe assembly 12. In this embodiment, which illustrates a device 10 in the bipolar mode, includes a first, proximal array of electrodes tines 30 and a second, distal array of electrode tines 40. The proximal array of electrode tines 30 exits the interior lumen (not shown) of the cannula 16 via a first plurality or set of staggered passageways or slots 34. The first plurality of staggered slots 34 is arranged proximally along the length of the cannula 16. The number, positioning, and orientation of the staggered slots 34 may be as described herein. The distal array of electrode tines 40 exits the interior lumen of the cannula 16 via a second plurality or set of staggered passageways or slots 42. These slots 42, like their proximal counterparts are also staggered about the periphery of the cannula 16. The proximal and distal slots 34, 42 may be oriented around the exterior of the cannula 16 in the same positions or they may be offset from one another in the radial direction.

In the bipolar embodiment of FIG. 7, one set of electrode tines (e.g., distal array of tines 40) acts as the active electrode while the other set of electrode tines (e.g., proximal array of tines 30) acts as the return electrode. During operation, RF energy travels in the direction of the arrows B in FIG. 7 from the active electrode array 40 to the return electrode array 30. Due to the staggered configuration of the slots 34, 42, there is a shorter path length or travel distance between adjacent, inner tine arrays 30' and 40'. The staggered configuration also has the additional benefit that the RF energy path is then is then echoed or "stretched" to the outermost tine arrays 30" and 40". This stretching of the RF energy path to the outermost tine arrays 30" and 40" is illustrated by the arrows C in FIG. 7. The stretching of the RF energy path using the staggered slots 34, 42 permits the formation of larger ablation zones as compared with conventional (non-staggered) bipolar devices.

An investigation of the bipolar, staggered design illustrated in FIG. 7 was compared with a conventional, non-staggered bipolar device. The non-staggered bipolar device used for comparison was the CONCERTO™ needle electrode device (Boston Scientific Scimed, Inc., Maple Grove, Minn.). Both devices were used to ablate test regions or zones within pig liver tissue. The staggered probe assembly 12 used tine arrays 30, 40 having a deployed diameter of around 3.5 cm. The non-staggered ablation probe used tine arrays having deployed diameters of 3.0 cm. RF energy was then applied to the respective electrode arrays in each device and the ablation time and dimensions were compared. Table 1 below lists the results of the comparison test

TABLE 1

|  | Staggered Bipolar Array | Serial (Non-Staggered) Bipolar Array |
| --- | --- | --- |
| Dimension Width | 5.0 cm | 3.5 cm |
| Dimension Length | 6.0 cm | 5.0 cm |
| Total Ablation Time | 9-10 minutes | 14-16 minutes |

As seen above, the staggered bipolar array design created an ablation having a longer length (+1.0 cm) and a larger width (+1.5 cm) as compared with the CONCERTO™ device. While the size of the array in the staggered design was slightly larger (+0.5 cm) than the array used in the CONCERTO™ device, the resultant width of the ablation was significantly larger (+1.5 cm). Moreover, the staggered bipolar array produced a larger ablation within a shorter period of time. Thus, the staggered bipolar probe assembly 12 of the type illustrated in FIG. 7 produces larger ablation zones within a shorter period of time. This is advantageous because the RF ablation device 10 can produce relatively wide margins around the target tissue zone or region (e.g., cancerous tissue).

Figure 8:
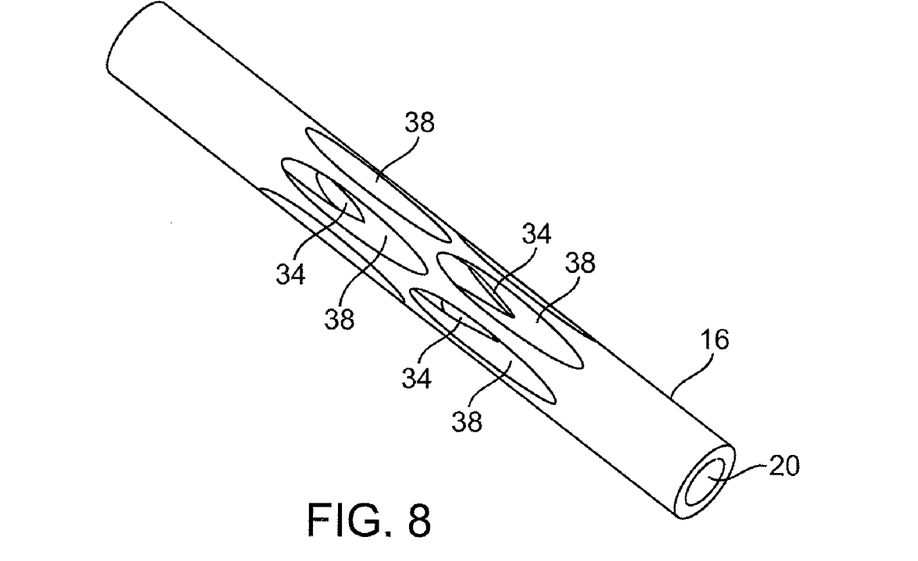
FIG. 8 illustrates a perspective view of a segment of cannula having angled or slanted slots arranged in a staggered fashion around the periphery of the cannula. The slots have variable, decreasing diameters.

FIG. 8 illustrates a perspective view of a cannula 16 having a plurality of passageways 34 according to one alternative aspect of the invention. In this embodiment, the passageways 34 are formed at an angle with respect to the longitudinal axis of the cannula 16 in the manner illustrated in FIG. 6B. The passageways 34 illustrated in this embodiment are shown with a variable diameter. The portion of the passageway 34 that is closest to the interior lumen 20 of the cannula has the narrowest diameter while the portion of the passageway 34 that is furthest from the interior lumen 20 has the largest diameter. In this regard, the passageway 34 flares outward with an increasingly large diameter. By having a reduced diameter passageway at one portion of the passageway 34 a seal is formed between the exterior of the electrode tine 30, 40 and the interior surface 38 of the passageway 34. In this regard, bodily fluids, tissue, and the like is prevented from entering the interior lumen 20 of the cannula 16 which could cause the moveable electrode member 22 to bind or seize. This sealing configuration can be maintained while the electrode array 30, 40 is in the fully retracted state. In yet another alternative embodiment, the portion of the passageway 34 that is closest to the interior lumen 20 of the cannula 16 has the largest diameter while the portion of the passageway 34 that is located furthest from the interior lumen 20 of the cannula 16 has the smallest diameter. This alternative embodiment has the same sealing benefits as the prior embodiment, the difference is that the passageway 34 flares inwardly to a larger diameter.

FIG. 9 illustrates a cross-sectional view of a cannula 16 according to another aspect of the invention. In this embodiment, the cannula 16 contains a plurality of passageways 34 that are slanted or angled with respect to the longitudinal axis of the cannula 16. In this embodiment, unlike the embodiment illustrated in FIG. 8, the passageways 34 have a substantially constant or continuous diameter from the entry point to the interior lumen 20 until the exit point on the exterior surface of the cannula 16. FIG. 9 illustrates a plurality of electrode tines 30 in the deployed state.

In the embodiment of FIG. 9, the illustrated electrode array 30 is coupled to a slidable electrode member 22. The electrode member 22 may be formed as a hollow length of tubing (e.g., hypotube) as is shown in FIG. 9. The individual electrode tines 30 may be bonded or otherwise secured to the distal end of the electrode member 22. As seen in FIG. 9, a second, inner conductor 23 is disposed within the outer electrode member 22. The inner conductor 23 is electrically isolated from the electrode member 22 by, for example, the presence of an insulator on the exterior of the inner conductor 23. The inner conductor 23 is, in turn, electrically coupled with another array of electrode tines (e.g., distal tines 40 as shown in FIG. 7).

While the staggered cannula 16 described herein has primary applications with RF ablation devices it should be understood that the staggered cannula 16 can also be used with other applications where tines need to be deployed. For example, the staggered arrangement of slots may be used with baskets, cages, snares, and the like.

While embodiments of the present invention have been shown and described, various modifications may be made without departing from the scope of the present invention. The invention, therefore, should not be limited, except to the following claims, and their equivalents.

What is claimed is:

1. A radiofrequency ablation device comprising:
an elongate cannula having a lumen disposed interiorly of an external wall, the elongate cannula including a plurality of slots formed within the external wall and providing access to the lumen; and
an electrode member slidably disposed within the elongate cannula, the electrode member including a plurality of tines configured for passage through the plurality of slots, wherein the plurality of slots are disposed in a staggered arrangement about the external wall of the cannula,
wherein the plurality of tines and the plurality of slots are configured such that a seal is formed between an exterior surface of the tines and an interior surface of the slots, wherein the slots comprise flared passageways, wherein each of the passageways comprises a portion that is closest to the interior lumen of the cannula and a portion that is furthest from the interior lumen of the cannula, and wherein a diameter of the portion that is closest to the interior lumen is different from a diameter of the portion that is furthest from the interior lumen.

2. The device of claim 1, wherein the staggered arrangement includes N slots disposed about the periphery of the external wall at a first longitudinal location and N slots disposed about the periphery of the external wall at a second longitudinal location.

3. The device of claim 2, wherein the slots disposed at the first longitudinal location at least partially overlap with the slots disposed at the second longitudinal location.

4. The device of claim 2, wherein the slots disposed at the first longitudinal location are positioned from the slots disposed at the second longitudinal location in a non-overlapping arrangement.

5. The device of claim 1, including a first set of staggered slots disposed on the external wall of the cannula at a first location and a second set of staggered slots disposed on the external wall at a second location, the first set of staggered slots configured to receive a first array of electrode tines and the second set of staggered slots configured to receive a second array of electrode tines.

6. The device of claim 1, wherein each slot disposed about the external wall is separated by at least 0.02 inches.

7. The device of claim 1, wherein the plurality of slots comprise passageways that are angularly oriented with respect to a central axis of the cannula.

8. The device of claim 1, wherein the slots comprise passageways having variable diameters.

9. The device of claim 1, further comprising an RF energy source configured to connect to the electrode member.

10. The device of claim 1, wherein the cannula comprises a metallic tube.

11. The device of claim 1, wherein the cannula comprises a polymer tube.

12. The device of claim 1, wherein the cannula has an outer diameter within the range of about 0.058 inches to about 0.1340 inches.

13. A radiofrequency ablation device comprising:
an elongate cannula having a lumen disposed interiorly of an external wall, the elongate cannula including a plurality of proximally and distally disposed passageways formed within the external wall of the cannula and providing access to the lumen, wherein the plurality of proximal and distal passageways are disposed in a staggered arrangement about the external wall of the cannula; and
an electrode member slidably disposed within the elongate cannula, the electrode member including a first plurality of tines configured for passage through the plurality of proximally disposed passageways and a second plurality of tines configured for passage through the plurality of distally disposed passageways,
wherein the first plurality of tines and the plurality of proximally disposed passageways are configured such that a seal is formed between an exterior surface of the first plurality of tines and an interior surface of the plurality of proximally disposed passageways,
wherein the second plurality of tines and the plurality of distally disposed passageways are configured such that a seal is formed between an exterior surface of the second plurality of tines and an interior surface of the plurality of distally disposed passageways, and wherein each of the proximally and distally disposed passageways comprises a portion that is closest to the interior lumen of the cannula and a portion that is furthest from the interior lumen of the cannula, and wherein each of the proximally and distally disposed passageways has a variable diameter with a diameter of the portion closest to the interior lumen being different from a diameter of the portion furthest from the interior lumen.

14. The device of claim 13, wherein the cannula has an outer diameter within the range of about 0.058 inches to about 0.1340 inches.

15. The device of claim 13, further comprising an RF energy source configured to connect to the electrode member.

16. The device of claim 13, wherein when the electrode member is retracted in a proximal state, the first plurality of tines and the second plurality of tines are at least partially disposed within the proximally and distally disposed passageways, respectively.

17. The device of claim 13, wherein the plurality of proximal and distal passageways disposed about the external wall of the cannula are aligned in the same positions about the external wall of the cannula.

18. The device of claim 13, wherein the plurality of proximal and distal passageways disposed about the external wall of the cannula are aligned in offset positions about the external wall of the cannula.

19. The device of claim 1, wherein the diameter of the portion of the passageways that is closest to the interior lumen of the cannula is smaller than the diameter of the portion of the passageways that is furthest from the interior lumen of the cannula, such that the passageways flare outward with an increasingly large diameter.

20. The device of claim 13, wherein the diameter of the portion of the passageways that is closest to the interior lumen of the cannula is smaller than the diameter of the portion of the passageways that is furthest from the interior lumen of the cannula, such that the passageways flare outward with an increasingly large diameter.

* * * * *